United States Patent [19]

Paciello et al.

[11] Patent Number: 5,717,126
[45] Date of Patent: Feb. 10, 1998

[54] PHOSPHOROUS-CONTAINING CALIXARENES

[75] Inventors: Rocco Paciello, Bad Dürkheim; Michael Röper, Wachenheim; Heinz-Josef Kneuper, Mannheim; Ernst Langguth, Kirchheim; Peter Michael Lorz, Mannheim, all of Germany

[73] Assignee: BASF Aktiengesellschaft, Ludwigshafen, Germany

[21] Appl. No.: 505,220

[22] PCT Filed: Jun. 20, 1994

[86] PCT No.: PCT/EP94/01999

§ 371 Date: Aug. 7, 1995

§ 102(e) Date: Aug. 7, 1995

[87] PCT Pub. No.: WO95/00525

PCT Pub. Date: Jan. 5, 1995

[30] Foreign Application Priority Data

Jun. 25, 1993 [DE] Germany ............... 43 21 194.1

[51] Int. Cl.$^6$ ............... C07F 9/6574; C07C 45/49
[52] U.S. Cl. ............... 558/78; 558/77; 568/454
[58] Field of Search ............... 558/77, 78; 568/454

[56] References Cited

U.S. PATENT DOCUMENTS 4,416,829  11/1983  Lee et al. ............... 558/78

FOREIGN PATENT DOCUMENTS 0 353 770  2/1990  European Pat. Off.
0 487 036  5/1992  European Pat. Off.

OTHER PUBLICATIONS

Khasnis, D.V. et al. Chemistry in Molecular Baskets: Variable Coordination of Phosphorus in Calix[4]arenes. Phosphorus, Sulfur, and Silicon, 1993, 75, 253–256.

*Primary Examiner*—Michael G. Ambrose
*Attorney, Agent, or Firm*—John H. Shurtleff

[57] ABSTRACT

Phosphorus-containing calixarenes of the general formula I

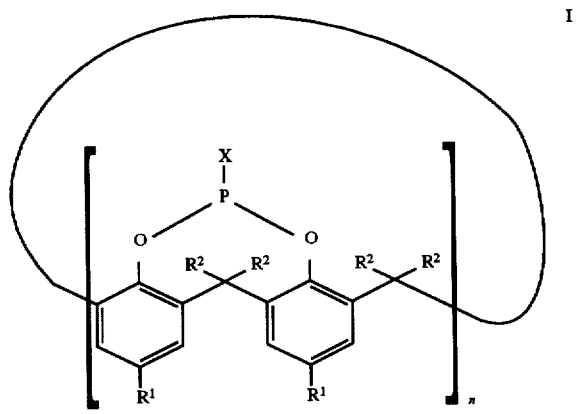

and a process for their preparation are described. Additionally, a process for the preparation of aldehydes by the hydroformylation of $C_3$–$C_{20}$-olefins by means of rhodium or ruthenium carbonyl complexes, in which the phosphorus-containing calixarenes of the formula I are used as ligands, is described.

11 Claims, No Drawings

PHOSPHOROUS-CONTAINING CALIXARENES

This application was filed under 35 U.S.C. 371 and was based upon PCT International Application No. PCT/EP94/ 01999, which was filed on Jun. 20, 1994.

The present invention relates to phosphorus-containing calixarenes.

Carbonylation reactions are understood as meaning the production of oxygen-containing products by reacting an organic compound with carbon monoxide and preferably a further reactant, especially hydrogen, in the presence of a catalyst. An industrially particularly important reaction is the hydroformylation of olefins by reaction with carbon monoxide and hydrogen with formation of aldehydes which contain one carbon atom more than the starting materials. The catalysts used are group VIII transition metal complexes which contain phosporus-containing ligands, for example phosphites (cf. J. Falbe, New Synthesis with Carbon Monoxide, Springer Verlag, New York 1980).

In addition to cobalt catalysts rhodium catalysts have in recent years become increasingly important for the hydroformylation of lower α-olefins, since they permit reaction at a lower pressure. As a rule, triphenylphosphine is used in excess as the phosphorus ligand, a high ligand/rhodium ratio being required in order to increase the selectivity of the reaction to give the commercially desired n-aldehyde product.

In recent years, attempts have been made to obtain more effective phosphorus ligands for the hydroformylation. In addition to phosphites having different substituents, phosphites too were tested for their suitability as catalysts. When these form a coordinate bond with a transition metal center, phosphites give catalysts having higher activity, but the life of these catalyst systems is unsatisfactory owing to the considerable sensitivity of the phosphite ligands to hydrolysis. Bisaryldiol-substituted chelating polyphosphites, as described in EP-A 21 46 22, are said to have dramatically reduced sensitivity to hydrolysis. The rhodium complexes of these ligands are said to form extremely active hydroformylation catalysts. EP-A 213 639 describes chelate bisphosphites which have diorganophosphite functionality at one phosphorus atom and triorganophosphite functionality at the second phosphorus atom. EP-A 155 508 furthermore discloses the use of bis-aryldiol-substituted monophosphites in the rhodium-catalyzed hydroformylation of sterically hindered olefins, eg. isobutene. EP-A 472 071 discloses chelate bisphosphite ligands in which bis-aryldiols are linked via bisphosphite ester bridges to alkane-diols or o-aryldiols. Finally, diol- and triol-substituted mono-phosphites and their use in hydroformylation are described in EP-A 149 894, EP-A 96 988 and EP-A 96 986.

In the hydroformylation of olefins, depending on the double bond position at which the carbon monoxide undergoes addition, straight-chain aldehydes, which are referred to as n-aldehydes, or branched aldehydes, ie. isoaldehydes, are formed. This is shown schematically in equation (1):

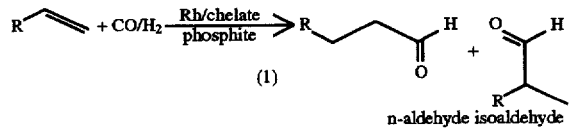

(1)

However, it is generally desirable for the fraction of n-aldehyde, referred to below as n-fraction, to be as large as possible compared with that of the isoaldehyde in the hydroformylation product, since the n-aldehydes lead to products having particularly advantageous plasticizer properties in the further processing of the aldehydes to plasticizer alcohols and plasticizers (cf. for example U.S. Pat. No. 4,426,542).

When the chelate bisphosphite ligands of the abovementioned prior art are used, hydroformylation products having a very high n-fraction of up 96% are obtained in the rhodium-catalyzed hydroformylation of olefins.

It is an object of the present invention to provide ligands for the rhodium- or ruthenium-catalyzed hydroformylation of olefins, with the aid of which the n-fraction in the hydroformylation product can be even further increased.

We have found that this object is achieved by phosphorus-containing calixarenes of the general formula I

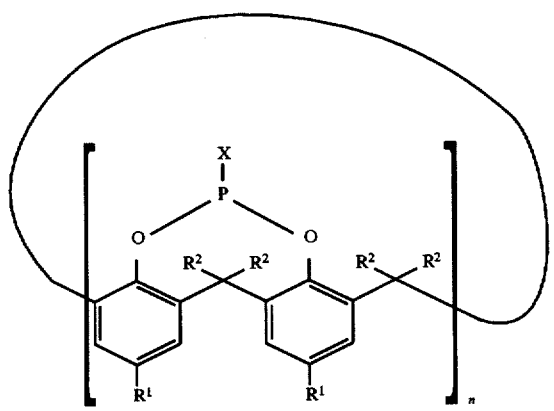

where n is an integer from 2 to 4, $R^1$ is hydrogen, $C_1$–$C_{20}$-alkyl, $C_1$–$C_{20}$-alkoxy, sulfonate or carboxylate, the radicals $R^2$ are identical or different and are hydrogen or $C_1$–$C_{20}$-alkyl and X is hydrogen, $C_1$–$C_{20}$-alkyl, $C_1$–$C_{20}$-alkoxy or a phenyl or phenoxy group which is unsubstituted or substituted by 1 to 3 $C_1$–$C_{20}$-alkyl, $C_1$–$C_{20}$-alkoxy, sulfonate, carboxylate, $C_1$–$C_{20}$-alkylthio and/or $C_2$–$C_{20}$-dialkylamino groups.

We have also found a process for the preparation of phosphorus-containing calixarenes of the formula I, which comprises reacting a calixarene of the general formula IV

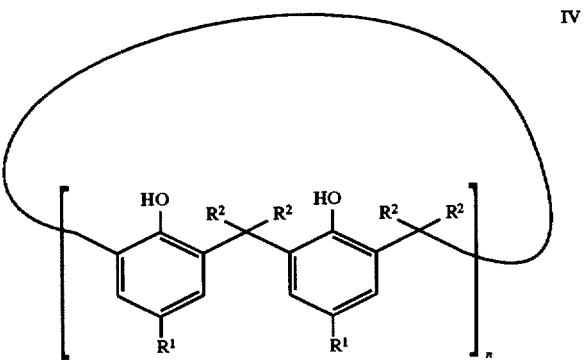

where n, $R^1$ and $R^2$ have the abovementioned meanings, with a phosphorus compound of the general formula V $XPHal_2$      V where X has the abovementioned meanings and Hal is fluorine, chlorine, bromine or iodine, in the presence of a base.

We have also found a process for the preparation of aldehydes by the hydroformylation of $C_2$–$C_{20}$-olefins by means of a $CO/H_2$ gas mixture in the presence of rhodium carbonyl complexes or ruthenium carbonyl complexes with a phosphorus-containing ligand and in the presence of a solvent, which comprises using the phosphorus-containing calixarenes of the formula I as ligands.

The novel phosphorus-containing calixarenes are cyclic phosphites and phosphonites of hydroxylated calixarenes.

In the novel phosphorus-containing calixarenes of the general formula I, $R^1$ may be hydrogen or $C_1$–$C_{20}$-alkyl, preferably $C_1$–$C_6$-alkyl, $C_1$–$C_{20}$-alkoxy, preferably $C_1$–$C_6$-alkoxy, sulfonate or carboxylate. $R^1$ is particularly preferably tert-butyl, sulfonate or carboxylate.

In the novel phosphorus-containing calixarenes of the formula I, the radicals $R^2$ may be identical or different and are hydrogen or $C_1$–$C_{20}$-alkyl, preferably $C_1$–$C_6$-alkyl. $R^2$ is particularly preferably hydrogen.

In the novel phosphorus-containing calixarenes of the formula I, X may be hydrogen, $C_1$–$C_{20}$-alkyl, preferably $C_1$–$C_6$-alkyl, $C_1$–$C_{20}$-alkoxy, preferably $C_1$–$C_6$-alkoxy, or a phenyl or phenoxy group which is unsubstituted or substituted by 1 to 3, preferably 1 or 2, $C_1$–$C_{20}$-alkyl, preferably $C_1$–$C_6$-alkyl, $C_1$–$C_{20}$-alkoxy, preferably $C_1$–$C_6$-alkoxy, $C_1$–$C_{20}$-alkylthio, preferably $C_1$–$C_6$-alkylthio, $C_2$–$C_{20}$-dialkylamino, preferably $C_2$–$C_{10}$-dialkylamino, sulfonate or carboxylate groups. Preferred phosphorus-containing calixarenes are those in which X is phenoxy of the general formula II

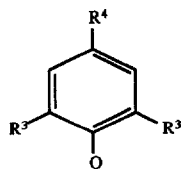

II where $R^3$ and $R^4$ may be identical or different and may each be hydrogen, $C_1$–$C_{20}$-alkyl, preferably $C_1$–$C_6$-alkyl, $C_1$–$C_{20}$-alkoxy, preferably $C_1$–$C_6$-alkoxy, $C_1$–$C_{20}$-alkylthio, preferably $C_1$–$C_6$-alkylthio, and/or $C_2$–$C_{20}$-dialkylamino, preferably $C_2$–$C_{10}$-dialkylamino, and $R^4$ may additionally be sulfonate or carboxylate.

The sulfonate and carboxylate groups in the novel calixarene derivatives may be present both in protonated form, ie. as sulfo or carboxyl groups; preferred calixarenes are those in which these groups are present in salt form, for example as alkali metal, alkaline earth metal or onium salt, in particular as ammonium or phosphonium salt. The presence of sulfonate or carboxylate groups in the novel phosphorus-containing calixarenes increases their water solubility and thus facilitates the hydroformylation in an aqueous medium.

A particularly preferred phosphorus-containing calixarene is that of the formula III.

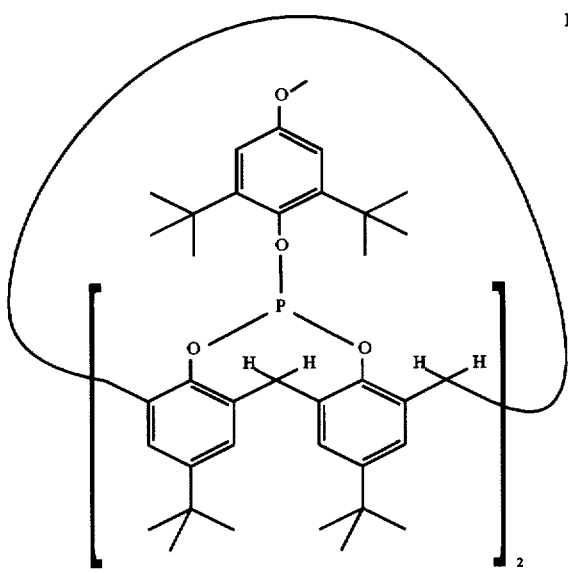

The novel phoshorus-containing calixarenes can be obtained by reacting a hydroxyl-carrying calixarene of the general formula IV

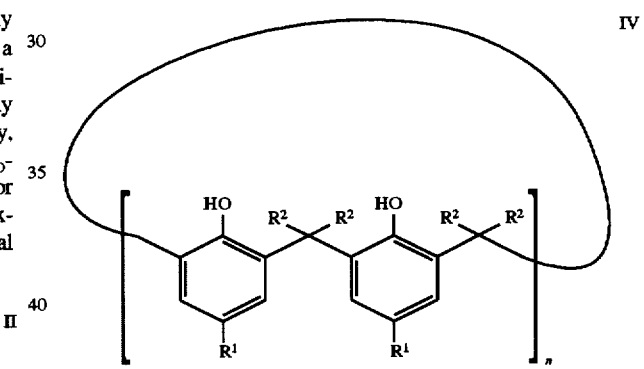

where n, $R^1$ and $R^2$ have the abovementioned meanings, with a phosphorus compound of the general formula V XPHal$_2$    V where X has the abovementioned meanings and Hal is fluorine, chlorine, bromine or iodine, preferably chlorine, in the presence of a base.

Calixarenes are defined as cyclic condensates of para-substituted phenols and aldehydes, preferably formaldehyde (cf. Chemie in unserer Zeit 25 (1991), 195). They can be prepared by processes known per se, as described, for example, in Gutsche, "Calixarenes", Chapter 2, pages 27 to 66, The Royal Society of Chemistry, Cambridge 1989.

The phosphorus-containing compounds of the formula V which are required for the preparation of the calixarene phosphites can be prepared by processes known per se (cf. Houben Weyl, Methoden der Org. Chemie, Volume XII/2, Chapter 2, Thieme, Stuttgart 1964), for example by reacting a phosphorus trihalide, such as phosphorus trichloride, phosphorus tribromide or phosphorus triiodide, with an alcohol or phenol in the presence of a base, such as an alkali metal or alkaline earth metal hydroxide or carbonate or preferably a tertiary amine.

The phosphorus-containing compounds of the formula V which are required for the preparation of the calixarene phosphonites can likewise be produced by known methods (cf. Houben-Weyl, Methoden der Org. Chemie, Volume XII/1, pages 302–318, Thieme, Stuttgart 1963), for example by reacting a phosphorus trihalide, such as phosphorus trichloride, with an aromatic compound, such as benzene, in the presence of a Friedel-Crafts catalyst, such as aluminum chloride.

For the preparation of the novel calixarene derivatives, the relevant calixarenes IV are reacted with, preferably, stoichiometric amounts of phosphorus-containing compound V per monomer unit of the calixarene used. The formula unit as shown in the square brackets in formula IV is defined as a monomer unit of the calixarene.

The reaction of the calixarene IV with the phosphorus compound V is carried out in the presence of a base.

The bases used may be mineral bases, for example alkali metal or alkaline earth metal oxides, alkali metal or alkaline earth metal hydroxides or alkali metal or alkaline earth metal carbonates, but the reaction is preferably carried out in the presence of tertiary amines, preferably tertiary aliphatic amines of 3 to 30 carbon atoms, for example trimethylamine, triethylamine, tri-n-propylamine, ethyldiisopropylamine, triisopropylamine, tributylamine, etc. The base is added in a molar ratio of from 1 to 200, preferably from 1.5 to 100, particularly preferably from 2 to 10, based on the amount of the phosphorus compound V used.

The preparation of the novel calixarene derivatives is advantageously carried out in a solvent. The solvent used may be any solvent which is inert under the reaction conditions, preferably aromatic hydrocarbons, such as benzene, toluene or xylene, or ethers such as diethyl ether, diisopropyl ether, methyl tert-butyl ether, tetrahydrofuran, dioxane, ethylene glycol dimethyl ether, etc.

The reaction is carried out in general at from −40°0 to 100° C. The pressure used is in general not critical for the reaction, but atmospheric pressure or the autogenous pressure of the reaction system is advantageously employed.

The novel phosphorus-containing calixarenes serve as ligands for rhodium and ruthenium in the rhodium- or ruthenium-catalyzed hydroformylation of $C_3$–$C_{20}$-olefins. The olefins used may be olefins having internal double bonds, α-olefins preferably being hydroformylated by the present process.

The rhodium and the ruthenium are introduced into the novel process in a conventional manner in the form of salts, for example as rhodium or ruthenium acetate or acetonylacetonate, as rhodium oxide or ruthenium oxide or as rhodium or ruthenium carbonyls. The type of compound in which the rhodium or ruthenium is used in the novel process is in general not critical since, under the hydroformylation conditions used and in the presence of the $CO/H_2$ reaction gas, these compounds are all converted into the catalytically active rhodium or ruthenium species which are homogeneously dissolved in the hydroformylation medium and are then complexed and stabilized by the phosphorus-containing calixarenes. The chemical nature of these catalytically active rhodium and ruthenium species could not be definitively determined, although there are a number of ideas among those skilled in the art with regard to their chemical structure, although it has not been possible finally to prove all of them.

Since the catalytically active rhodium or ruthenium compounds are genuine catalysts, ie. remain virtually completely unconsumed in the reaction and as such have high activity, very small amounts of rhodium or ruthenium compounds are sufficient for catalyzing the hydroformylation with satisfactory conversion. In general, the molar ratio of rhodium or ruthenium to the olefin used is from 1:1000 to 1:50,000, preferably from 1:1000 to 1:5000, in the steady-state reaction.

In the case of the novel phosphorus-containing calixarenes used, the molar ratio of calixarene to rhodium or ruthenium is in general from 1:1 to 100:1, preferably from 1:1 to 20:1, particularly preferably from 1:1 to 5:1.

The $CO/H_2$ molar ratio of the $CO/H_2$ mixture fed to the hydroformylation may be from 20:1 to 1:20, preferably from 1:1 to 20:1, particularly preferably 1:1.

The novel hydroformylation process is generally carried out in the presence of a solvent. The solvent used may be virtually any solvent which is inert under the hydroformylation conditions, for example hydrocarbons, esters or alcohols, but the aldehydes which are formed in the hydroformylation of the relevant olefin are preferably used as solvents in the hydroformylation. Other particularly preferred solvents are high boilers, ie. mixtures of high-boiling compounds, such as those formed during the hydroformylation reaction as byproducts in a number of secondary reactions, such as aldol condensations, eliminations, disproportionations and hydrogenations, from the aldehydes formed during the hydroformylation. A number of such high boilers and the method of their formation are described by way of example in U.S. Pat. No. 4,148,830 for the preparation of butyraldehyde.

The novel process is carried out in general at from 30° to 150° C., preferably from 60°0 to 130° C., particularly preferably from 90° to 110° C., and at in general from $1 \times 10^3$ to $1 \times 10^7$, preferably from $1 \times 10^5$ to $5 \times 10^6$, particularly preferably from $5 \times 10^5$ to $3 \times 10^6$, Pa.

The novel hydroformylation process can be carried out batchwise but is preferably operated continuously. Conventional process engineering, as described, for example, in U.S. Pat. No. 4,148,830, U.S. Pat. No. 4,329,511 or EP-A 313 559, may be used.

With the novel phosphorus-containing calixarenes as ligands for the catalytically active rhodium or ruthenium compounds, the n-fraction in the hydroformylation product can surprisingly be increased to 99.5% in the novel hydroformylation process.

EXAMPLES

Preparation of Phosphorus-Containing Calixarene
III

Stage 1:

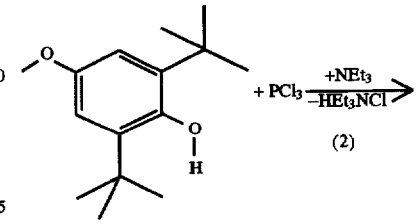

(2)

Stage 1:

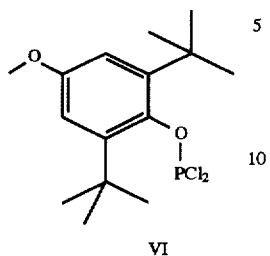

23.6 g (0.1 mol) of 3,5-di-tert-butyl-4-hydroxyanisole (commercially available or preparable according to J. Am. Chem. Soc. 77 (1955), 1672) were dissolved in 500 ml of toluene, and 50 ml of toluene were distilled off from this mixture. 68.2 ml (0.5 mol) of triethylamine were added to the cooled solution at room temperature, and the mixture was then metered into a solution, pre-cooled to −40° C., of 8.8 ml (0.1 mol) of phosphorus trichloride in 1 l of toluene. The solution was slowly warmed up to room temperature, stirred for 1 hour at room temperature and then heated at 100° C. for a further 10 hours. The resulting solution of the compound VI was fed in this form to stage 2.

Stage 2:

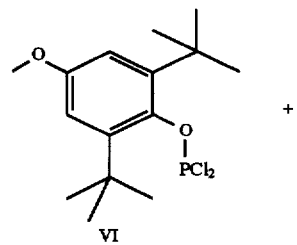

+

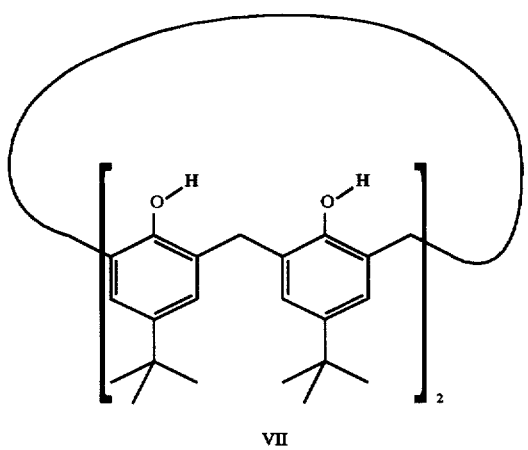

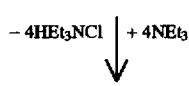

-continued
Stage 2:

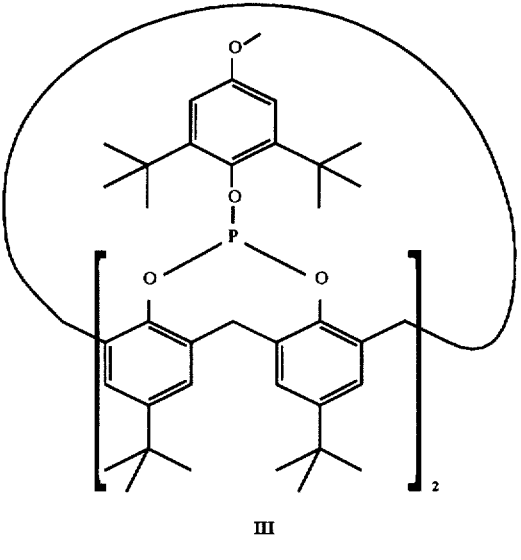

(3)

32.4 g (0.05 mol) of calix-4-arene VII (obtainable according to Gutsche "Calixarenes", Chapter 2, pages 27–66) were added in powder form to the solution of compound VI from the 1st stage, and this mixture was cooled to −40° C. A solution of 136.5 ml (1 mol) of triethylamine in 500 ml of toluene was metered into this mixture. The reaction mixture was slowly warmed up to room temperature and stirred for 1 hour at room temperature and for a further 10 hours at 100° C. The precipitated triethylammonium chloride was then filtered off from the reaction solution and washed with toluene. The toluene was removed from the combined toluene extracts by distillation, a light brown, viscous residue remaining. This was washed with pentane and then extracted with 400 ml of acetonitrile under reflux. After a part of the residue had dissolved, the remaining powder was filtered off, washed with pentane and dried.

The $^1$H- and $^{13}$C-NMR spectra confirmed the structure according to formula III. In the $^{31}$P-NMR spectra, a signal was observed at 121 ppm, based on phosphoric acid as standard.

Elemental analysis [result (theory)]: C 75.5% (76.2%); H 8.3% (8.9%); O 10.9% (9.9%); P 5.3% (5.1%).

The mass spectrum of III had a molecular peak at 1176 Dalton as the main component.

Example 2

Hydroformylation of 1-octene

In a 0.35 l autoclave, a mixture of 56.9 g of 1-octene (508 mmol), 0.032 g (0.124 mmol) of rhodium in the form of the complex Rh(CO)$_2$(acac) (acac=acetylacetonate) and 0.7098 g (0.604 mmol) of the compound III in 70 ml of Texanol® (2,2,4-trimethylpentane-1,3-diol monoisobutyrate) is heated to 100° C., and a pressure of 2×10$^6$ Pa was established by passing a CO/H$_2$ mixture (CO/H$_2$ volume ratio=1:1) into the autoclave and was kept constant during the total duration of the reaction by further introduction of this gas mixture. After a reaction time of 8 hours, the hydroformylation mixture was analyzed by gas chromatography. The result of this analysis is shown in the table.

TABLE

| | | |
|---|---|---|
| int. $C_8$-olefins | 3.41% by weight | 0.0386 mol |
| 1-Octene | 16.58" | 0.1879 mol |
| Octane | 7.84" | 0.0873 mol |
| 2-Propylhexanal | 0.00" | |
| 2-Ethylheptanal | 0.00" | |
| 2-Methyloctanal | 0.11" | 0.0010 mol |
| n-Nonanal | 21.84" | 0.1952 mol |
| Texanol | 45.8" | |
| Others | 0.0" | |
| Total | 95.6" | |
| Conversion | | 63 mol % |
| Yield of nonanal | | 39 mol % |
| Yield of octane | | 17 mol % |
| Selectivity (based on 1-octene converted) | | |
| Nonanals | 61% | |
| Octane | 27% | |
| internal olefins | 12% | |

The molar ratio of 1-nonanal to the total amount of nonanals was 99.5:0.5.

By increasing the reaction time, the conversion can be further increased without any decrease in the n-aldehyde selectivity of the catalyst.

We claim:

1. A phosphorus-containing calixarene of the formula I

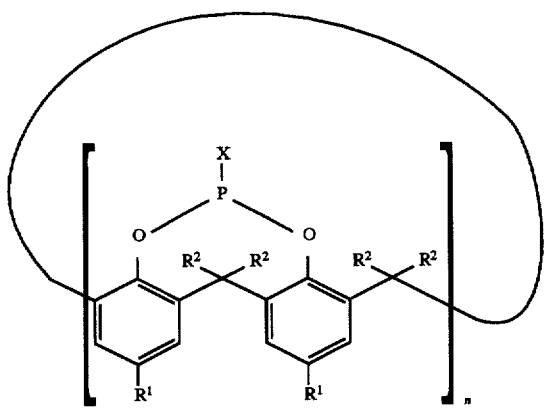

where n is an integer from 2 to 4, $R^1$ is hydrogen, $C_1$–$C_{20}$-alkyl, $C_1$–$C_{20}$-alkoxy, sulfonate or carboxylate, the radicals $R^2$ are identical or different and are hydrogen or $C_1$–$C_{20}$-alkyl and X is hydrogen, $C_1$–$C_{20}$-alkyl, $C_1$–$C_{20}$-alkoxy or a phenyl or phenoxy group which is unsubstituted or substituted by 1 to 3 $C_1$–$C_{20}$-alkyl, $C_1$–$C_{20}$-alkoxy, sulfonate, carboxylate, $C_1$–$C_{20}$-alkylthio or $C_2$–$C_{20}$-dialkylamino groups.

2. A phosphorus-containing calixarene as claimed in claim 1, in which X is phenyloxy of the formula II

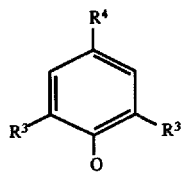

where $R^3$ and $R^4$ are identical or different and are each hydrogen, $C_1$–$C_{20}$-alkyl, $C_1$–$C_{20}$-alkoxy, $C_1$–$C_{20}$-alkylthio or $C_2$–$C_{20}$-dialkylamino and $R^4$ may additionally be sulfonate or carboxylate.

3. A phosphorus-containing calixarene as claimed in claim 2, in which $R^1$ is hydrogen, $C_1$–$C_6$-alkyl, $C_1$–$C_6$-alkoxy, sulfonate or carboxylate, and $R^2$ is hydrogen.

4. A phosphorus-containing calixarene as claimed in claim 1, of the formula III

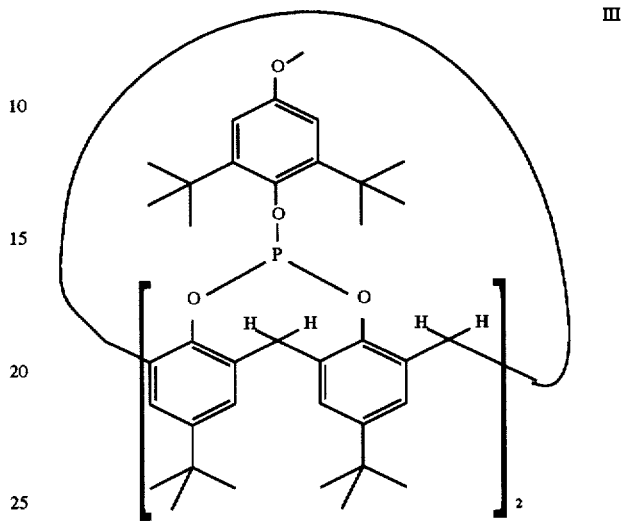

5. A process for the preparation of a phosphorus-containing calixarene as claimed in claim 1, which comprises reacting a calixarene of the formula IV

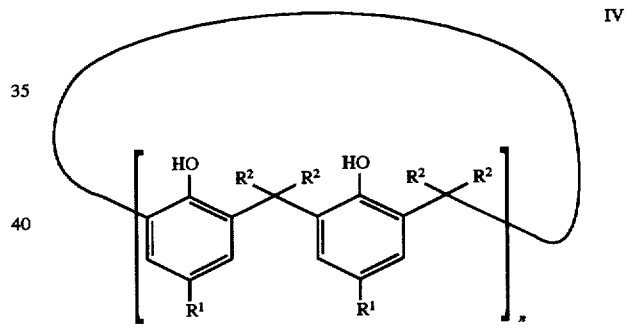

where n, $R^1$ and $R^2$ have the meanings stated in claim 1, with a phosphorus compound of the formula V $$XPHal_2 \quad V$$

where X has the meanings stated in claim 1 and Hal is fluorine, chlorine, bromine or iodine, in the presence of a base.

6. A process as claimed in claim 5, wherein the base used is a $C_3$–$C_{30}$-trialkylamine.

7. In a process for the preparation of an aldehyde by the hydroformylation of a $C_{10}$–$C_{20}$-olefin by means of a $CO/H_2$ gas mixture in the presence of a rhodium or ruthenium carbonyl complex with a phosphorus-containing ligand and in the presence of a solvent, the improvement which comprises carrying out the hydroformylation reaction in the presence of at least one phosphorous-containing calixarene as claimed in claim 1.

8. A process as claimed in claim 7, wherein the hydroformylation is carried out at from 30° to 150° C. and from $1 \times 10^3$ to $1 \times 10^7$ Pa.

9. A process as claimed in claim 7, wherein the solvent used is the aldehyde which is formed by the hydroformylation of the particular olefin reactant.

10. A process as claimed in claim 7, wherein the solvent used is a mixture of high-boiling compounds which are byproducts formed during the hydroformylation of an olefin reactant by secondary reactions of the resulting aldehyde product.

11. A process as claimed in claim 7, wherein an α-olefin is hydroformylated.

* * * * *